United States Patent [19]
Akai et al.

[11] Patent Number: 5,891,731
[45] Date of Patent: Apr. 6, 1999

[54] REAGENT FOR MEASURING RETICULOCYTES AND A METHOD OF MEASURING THEM

[75] Inventors: Yasumasa Akai; Yuji Itose; Kayo Hatanaka, all of Kobe; Takashi Sakata, Kakogawa, all of Japan

[73] Assignee: TOA Medical Electronics Co., Ltd., Hyogo, Japan

[21] Appl. No.: 843,260

[22] Filed: Apr. 14, 1997

[30] Foreign Application Priority Data

Apr. 12, 1996 [JP] Japan .................................. 8-091355

[51] Int. Cl.⁶ .......................... G01N 31/00; G01N 33/48
[52] U.S. Cl. .................................. 436/10; 436/8; 436/63; 436/164; 436/166; 436/172; 436/800; 252/408.1
[58] Field of Search .................................. 436/8, 10, 16, 436/18, 63, 164, 166, 172, 174, 176, 800; 435/2, 29, 30, 34, 39; 252/408.1

[56] References Cited

U.S. PATENT DOCUMENTS

| | | | |
|---|---|---|---|
| 4,146,604 | 3/1979 | Kleinerman | 435/40.51 |
| 4,882,284 | 11/1989 | Kirchanski et al. | 436/63 |
| 4,957,870 | 9/1990 | Lee et al. | 436/63 |
| 5,284,771 | 2/1994 | Fan et al. | 436/10 |
| 5,321,130 | 6/1994 | Yue et al. | 436/800 X |
| 5,360,739 | 11/1994 | Fan et al. | 436/63 |
| 5,496,734 | 3/1996 | Sakata | 436/63 |
| 5,534,416 | 7/1996 | Millard et al. | 436/34 |

FOREIGN PATENT DOCUMENTS

| | | |
|---|---|---|
| 0 545 314 A1 | 6/1993 | European Pat. Off. . |
| 0 634 640 A1 | 1/1995 | European Pat. Off. . |
| 0 767 382 A2 | 4/1997 | European Pat. Off. . |
| WO 94/18828 | 9/1994 | WIPO . |

OTHER PUBLICATIONS

Terstappen et al. "Multidimensional Flow Cytometric . . . " *Blood Cells,* vol. 17 (3), pp. 585–602, 1991.
Valet "A New Method For Fast Blood Cell Counting . . . " *BLUT,* vol. 49 (2), pp. 83–90, Aug. 1984.
Derwent Abstract—JP 61 079 163 A, Apr. 22, 1986.
Derwent Abstract—JP 62 153 758 A, Jul. 8, 1987.
Patent Abstracts of Japan—JP 08 338839, Dec. 24, 1996.
Linda G. Lee, Chia–Heui Chen, and Laura A. Chiu, "*Thiazole Orange: A New Dye for Reticulocyte Analysis,*" *Cytometry,* 7, pp. 508–517 (1986).

*Primary Examiner*—Maureen M. Wallenhorst
*Attorney, Agent, or Firm*—Bryan Cave LLP

[57] ABSTRACT

A reagent for measuring reticulocytes which has at least one dye which specifically stains reticulocytes and at least one dye which specifically stains leukocytes.

12 Claims, 4 Drawing Sheets

RBC (matured erythrocytes)
RET (reticulocytes)
PLT (platelet)
WBC (leukocytes)

REAGENT FOR MEASURING RETICULOCYTES AND A METHOD OF MEASURING THEM

BACKGROUND OF THE INVENTION

1. Field of the Invention

The present invention relates to a reagent for measuring reticulocytes and also to a method of measuring them. More particularly, it relates to a reagent for measuring reticulocytes and a reticulocyte maturation index in blood in the field of clinical tests and also to a method of measuring them.

2. Description of the Related Arts

Reticulocytes are young erythrocytes immediately after a release of denucleated erythroblastic cells in bone marrow into peripheral blood. Characteristics of reticulocytes are that, as traces of maturing steps of erythrocytes, they retain, as residual substances in their cells, cell organelles such as ribosome and mitochondria and a small amount of RNA, which are not contained in matured erythrocytes.

In the field of clinical tests, it is very important to classify and count reticulocytes for grasping hematopoietic state in bone marrow of patients. In a normal and healthy person where hematopoiesis in bone marrow is normal, the number of reticulocytes occupies 0.5–3.0% of total numbers of erythrocytes. However, in the case where the hematopoiesis in bone marrow is abnormal, for example, where the hematopoiesis in bone marrow is inhibited, the number of reticulocytes decreases, while where the hematopoiesis in bone marrow is promoted, the number of reticulocytes increases. To be more specific, it decreases during the course of chemotherapy for a plastic anemia and malignant tumor while they increase in the case of hemolytic anemia and the like.

One of conventional methods for counting reticulocytes is a manual method in which a blood sample is mixed with a staining solution containing a basic dye such as New Methylene Blue (NMB) or Brilliant Cresyl Blue (BCB) to precipitate and to stain the above-mentioned residual substances contained in reticulocytes and each cell is observed under a microscope to discriminate reticulocytes from matured erythrocytes.

However, there are problems in such a manual method that an operation of preparing the sample is troublesome, individual difference for the discrimination of the cells takes place among medical technician and the statistic error is big due to the fact that the number of counted cells is small.

In order to solve these problems, a method (flow cytometry) has been conducted. In said method, reticulocytes are subjected to fluorescence staining using a fluorescent basic dye instead of the above-mentioned basic dye, the forward scattered light intensity and fluorescence intensity of cells are measured by a flow cytometer and matured erythrocytes and reticulocytes are discriminated, classified and counted mostly by means of the difference in the fluorescence intensities between them. As the dye used for this method, Acridine Orange, Thiazole Orange, Auramine O, etc. are well known.

In addition, in this method, it is also possible to classify and count reticulocytes depending upon the degree of maturation by means of the fluorescence intensity of reticulocytes whereby the maturation index of reticulocytes can be calculated. Since it has been known that the proportion of reticulocytes having a high fluorescence intensity or the proportion of youngest reticulocytes is useful as an index for the recovery of hematopoietic ability of bone marrow, utilization of said method has been expected.

However, an argon laser which is very expensive and is large in size is required as a light source for exciting the fluorescent dye and, therefore, there is a problem that the apparatus itself becomes expensive and large too. In addition, the above-mentioned dyes which can be used for the flow cytometry except Auramine 0 require a staining time of five minutes or more for staining reticulocytes. Especially, it has been reported by Lee, L. G. et al: Cytometry; 7:508–517(1986) that Thiazole Orange requires a staining time of 60 minutes or more and, therefore, it is difficult to fully automate the preparation of the sample whereby there is a problem in view of economy of manpower. Thus, the preparation of the sample is carried out by hands and, therefore, there is a problem that the data will vary depending upon technique of a person who prepares the sample and that, especially in the case of the maturation index of reticulocytes, large difference in the data may occur.

In the U. S. Pat. No. 5,360,739, there is a disclosure on a flow cytometric method in which reticulocytes are determined by measuring scatter light intensity and absorbance or fluorescence intensity using a He/Ne laser which is a relatively cheap light source and Oxazin 750 as a dye. However, the problem of abnormal lymphocytes which will be mentioned later is not described there.

In the meanwhile, the present inventor has also conducted an intensive study on reagents and methods for accurate and quick measurement of reticulocytes and reticulocyte maturation index by use of a flow cytometric method with a less expensive and small light source but there is still a problem that, especially in samples from patients where leukocytes are abnormal in number or type, for example, abnormal lymphocytes appear, the fluorescence intensity of lymphocytes is nearly the same as that of reticulocytes and, therefore, discrimination between them is difficult. Accordingly, neither reagent nor method for accurate and quick measurement has been established so far for the case where the discrimination between leukocytes and reticulocytes is difficult. Incidentally, this fact is already suggested in an instruction manual for a Retic-Count™ which is a kit for measuring of erythrocytes by a flow cytometry using an argon laser as a light source and is available in the market already. In this manual, it is mentioned that, when a sample containing an abnormal increase in leukocyte number is measured, confirmation by another method is necessary.

SUMMARY OF THE INVENTION

The present invention provides a reagent for measuring reticulocytes comprising at least one dye which specifically stains reticulocytes and at least one dye which specifically stains the leukocytes.

Also, the present invention provides a method for measuring reticulocytes using the above-mentioned reagent.

DETAILED DESCRIPTION OF THE PREFERRED EMBODIMENTS

Figure 1:
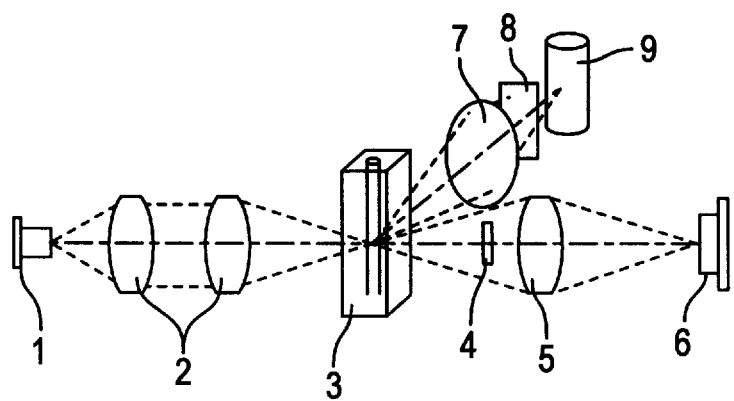
FIG. 1 is a drawing which shows optical parts of a flow cytometer having a light source of red wave length used in the measuring method of the present invention.

The present invention is to realize a reagent and a measuring method whereby reticulocytes can be accurately and quickly measured even in the case of an unusual sample as described above, e.g., a sample from a patient wherein a lot of abnormal lymphocytes appear. Even with a sample from a patient wherein a lot of abnormal leukocytes are present, the reagent can be used to accurately classify and count reticulocytes because the fluorescence intensity of leukocytes only is strengthened without changing the fluorescence intensity of matured erythrocytes and reticulocytes.

The reagent of the present invention comprises a dye which specifically stains reticulocytes and another dye which specifically stains the leukocytes. The dye which specifically stains reticulocytes means a dye which is capable of staining reticulocytes to such an extent that they can be discriminated from other blood cells and is, for example, a compound represented by the formula (I):

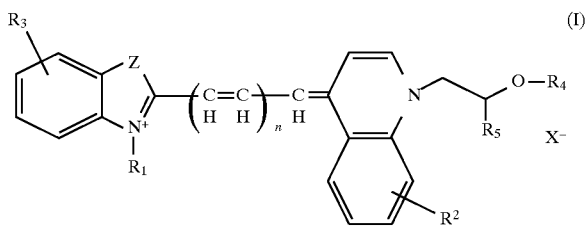

wherein $R_1$ is hydrogen atom or a lower alkyl group; $R_2$ and $R_3$ are, the same or different, hydrogen atom, a lower alkyl or lower alkoxy group; $R_4$ is hydrogen atom, an acyl or lower alkyl group; $R_5$ is hydrogen atom or an optionally substituted lower alkyl group; Z is sulfur atom, oxygen atom, or carbon atom substituted with a lower alkyl group; n is 1 or 2; and $X^-$ is an anion.

The lower alkyl group of $R_1$ in the formula (I) may be a straight or branched chain alkyl group having 1 to 6 carbon(s) such as methyl, ethyl, propyl, butyl, isobutyl, sec-butyl, tert-butyl, pentyl or hexyl group and, among them, methyl and ethyl group are preferred.

The lower alkyl group of $R_2$ and $R_3$ may be the same one as the above $R_1$ and the lower alkoxy group of $R_2$ and $R_3$ may be an alkoxy group having 1 to 6 carbon(s) such as methoxy, ethoxy or propoxy group and, among them, methoxy and ethoxy group are preferred. $R_2$ and $R_3$ may be substituted at ortho-, meta- or para- position. It is more preferred that both $R_2$ and $R_3$ are hydrogen atoms.

The acyl group of $R_4$ may be preferably derived from aliphatic carboxylic acids such as acetyl or propionyl group, among which acetyl group is more preferable. The lower alkyl group of $R_4$ may be the same as $R_1$.

The lower alkyl group of $R_5$ may be the same as $R_1$. The lower alkyl group of $R_5$ may be substituted with one to three hydroxyl group(s) or halogen atom(s) such as fluorine, chlorine, bromine and iodine. Among them, hydroxymethyl and hydroxyethyl group are preferred.

The lower alkyl group in Z may be the same as $R_1$. Preferably, Z is sulfur atom.

Examples of the anion of $X^-$ may be halogen ion (such as fluorine, chlorine, bromine and iodine ion), borohalide ion (such as $BF_4-$, $BCl_4-$ and $BBr_4-$), phosphorous compound ion, halooxy-acid ion, fluorosulfate ion, methyl sulfate ion and tetraphenylboron compound ion having halogen atom or a haloalkyl group as a substituent in a phenyl ring. Among them, bromine ion and $BF_4-$ are preferred.

Specific examples of the compound represented by the formula (I) may be as follows.

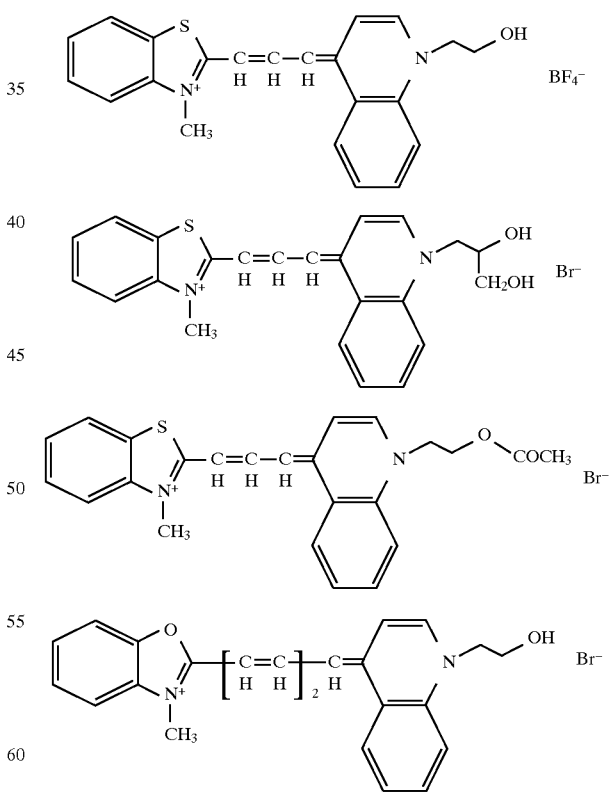

Among the above-mentioned compounds represented by the formula (I), the compounds in which n=1 can be synthesized, for example, by the reaction of the compound of the following formula:

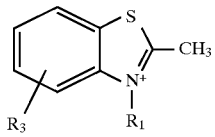

with N,N-di-substituted formamidine, followed by the reaction of the resulting intermediate with a quinoline derivative represented by the following formula:

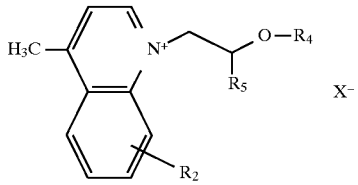

and then by treating with sodium borohydride. In this case, $R_2$ and $R_3$ may be substituted at ortho-, meta- or para-position. The substitutents are preferably hydrogen atom.

Further, the compounds of the formula (I) in which n=2 can be synthesized by using, for example, malondialdehyde bis(phenylimine) salt instead of N,N-di-substituted formamidine in the above-mentioned reaction.

Other examples of applicable dyes which may stain reticulocytes may be those represented by the following formula:

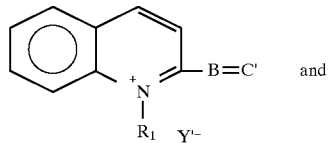

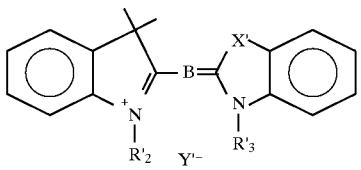

[in which, B is —(CH=CH)$_{n'}$—CH= (where n' is 0, 1 or 2) or —CH=C(—R$_{4'}$)—CH=; C' is

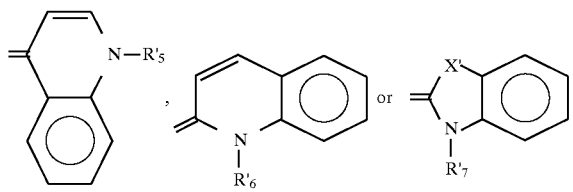

X' is O, S, Se or >C(CH$_3$)$_2$; Y' is Cl, Br or I; and R$_{1'}$, R$_{2'}$, R$_{3'}$, R$_{4'}$, R$_{5'}$, R$_{6'}$ and R$_{7'}$ are, the same or different, a lower alkyl, lower alkenyl or halogenated lower alkyl group.] such as:

(1) 1,1',3,3,3',3'-Hexamethylindodicarbocyanine iodide (available from HIDCI, Lambda Physik)

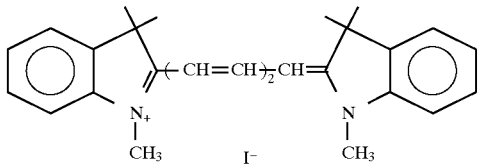

(2) 1,1'-Diethyl-2,4'-quinocarbocyanine iodide (NK-138; available from Nippon Kanko Shikiso Kenkyusho)

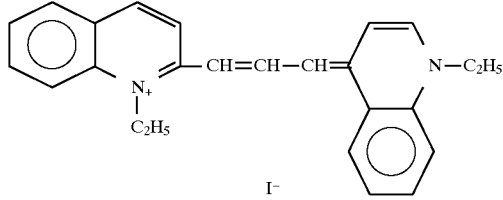

(3) Pinacyanol chloride

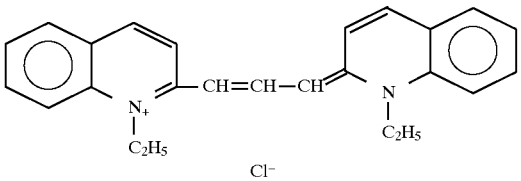

(4) 1,3'-Diethyl-2,2'-quinothiacarbocyanine iodide

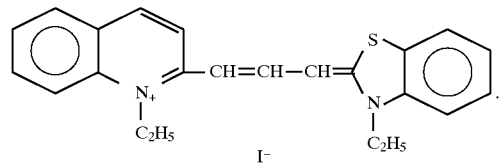

Furthermore, other known dyes for detection of reticulocytes such as Oxazin 750 may be used as well.

The amount of the above-mentioned dye in the reagent of the present invention is such that it is sufficient for staining reticulocytes, but it may be suitably adjusted depending upon the type of the dye and the composition of the reagent. It may be, for example, about 0.1–100 mg/liter to the total volume of the reagent, more preferably about 0.3–30 mg/liter or, still more preferably, 0.3–3 mg/liter.

The dyes which specifically stain leukocytes include those having the formula (II) or (III):

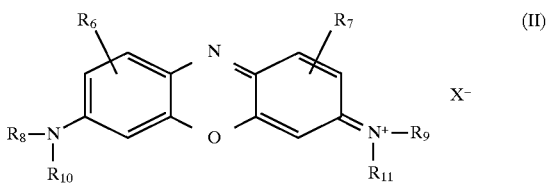

wherein $R_6$ and $R_7$ are, the same or different, hydrogen atom, a lower alkyl, lower alkoxy or phenyl group; $R_8$ to $R_1$ are, the same or different, hydrogen atom or a lower alkyl group; and $X^-$ is an anion.

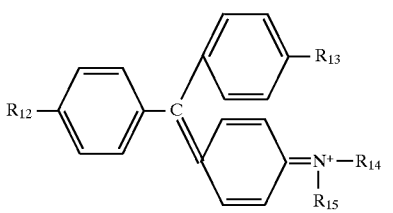

(III)

wherein $R_{12}$ and $R_{13}$ are, the same or different, hydrogen atom, a lower alkyl, lower alkoxy group or a lower-alkyl-substituted amino group; $R_{14}$ and $R_{15}$ are, the same or different, hydrogen atom or a lower alkyl group; and $X^-$ is an anion.

The lower alkyl and lower alkoxy groups in the above formula (II) and (III) may be the same as $R_1$.

Examples of anion $X^-$ are the same as described above. Among them, chlorine ion is preferred.

The above-mentioned dye is used in the reagent of the present invention in such a concentration that leukocytes can be sufficiently stained and the staining of reticulocytes with the dye for measuring reticulocytes is not disturbed. The concentration can be suitably adjusted depending upon the type of the dye and the composition of the reagent. For example, it may be about 0.001–200 mg/liter to the total volume of the reagent, more preferably about 0.003–3 mg/liter and, still more preferably, 0.003–0.03 mg/liter.

In the reagent of the present invention, the dye which specifically stains reticulocytes may quickly permeate into the erythrocytes to stain the RNA in the cells. Therefore, it is still possible to classify and count reticulocytes even by the sole use of the dye which specifically stains reticulocytes. However, in a special case where, for example, a lot of abnormal cells of a lymphocyte type appear due to acute lymphocytic leukemia or the like, the fluorescence intensities of both lymphocytes and immatured reticulocytes are nearly the same and, accordingly, it is difficult to discriminate them.

On the other hand, in the reagent of the present invention, the dye which specifically stains leukocytes is capable of specifically staining only leukocytes at the above-mentioned concentrations. It is likely the although the situation may vary depending upon the type of the dye, the dye which specifically stains the leukocytes will probably able to specifically stain the granular components and nuclei which are not contained in reticulocytes but are contained in leukocytes whereby the fluorescence intensity of leukocytes becomes stronger. As a result thereof, a clear difference is resulted between the fluorescence intensities of reticulocytes and leukocytes or, in other words, the fluorescence intensity of leukocytes becomes strong as compared with that of reticulocytes, while the fluorescence intensity of reticulocytes does not change whereby the discrimination of both is still possible even in the above-mentioned case.

The above-described examples of the dyes are capable of being excited by red wave length but the present invention is not limited thereto. The dye may be used in a combination with a dye which is capable of being excited by other wave length such as blue wave length and, even in such a case, it is still possible to improve the discrimination of reticulocytes from leukocytes.

The reagent of the present invention may further contain a polyvalent anion for inhibiting the nonspecific staining of erythrocytes, a buffer, an osmotic compensating agent and/or a staining promoter.

During the course of investigation on the composition of the reagent, the present inventors have found that, when NaCl (especially, Cl−) is used as a main component for osmotic compensating agent in a commonly used staining solution, the nonspecific fluorescence of erythrocytes is large while specific fluorescence of reticulocytes is small and, as a result, the discrimination between erythrocytes and reticulocytes becomes difficult. On the other hand, the inventors have also found that, when Cl− in the staining solution is substituted with a polyvalent anion, the nonspecific fluorescence of matured erythrocytes is significantly inhibited whereby the discrimination between erythrocytes and reticulocytes becomes easier. Accordingly, in the reagent of the present invention, it is preferred that the polyvalent anion is contained. As the polyvalent anion, sulfate ion, phosphate ion, carbonate ion and polycarboxylate ion are especially preferred and examples of compounds which are able to supply them are citric acid, sulfuric acid, phosphoric acid, EDTA and alkali metal salts thereof. These polyvalent anions may be used as a combination thereof. Concentration of the polyvalent anion in terms of its ratio to all of the anionic components in the reagent may be not less than 50% or, preferably, not less than 70%.

The reagent of the present invention may also contain a buffer to keep the pH constant. The buffer is used for keeping the pH constant whereby the stable staining result of reticulocytes is maintained. It may be used in a concentration of around several mM to 100 mM. There is no particular limitation as to the type of the buffer so far as it is commonly used and, for example, carboxylates, phosphates, Good's buffer, taurine, triethanolamine, etc. may be suitably used depending upon the desired pH. The suitable pH for the reagent of the present invention may vary depending upon the dyes used and may be within the range of 6.0–11.0, preferably 7.0–10.0 or, more preferably, 8.0–9.5. When the pH is lower than the above-mentioned range, erythrocytes become fragile and hemolysis is apt to take place whereby accurate measurement of reticulocytes becomes difficult. When the pH is higher than that, acidic functional groups on erythrocyte membrane are dissociated and, therefore, they are apt to be bound to the dye which is cationic whereby the nonspecific fluorescence of the erythrocytes increases. As a result thereof, there is a tendency that the discrimination between matured erythrocytes and reticulocytes becomes difficult and that is not preferred. When the above-mentioned polyvalent anion has a buffering ability to adjust the pH to a suitable range, it is possible to use said anion itself as a buffer.

The reagent of the present invention may also contain an osmotic compensating agent. It is desirable that the osmotic pressure of the reagent adjusted to a physiological osmotic pressure so that hypotonic hemolysis of erythrocytes can be prevented and, usually, said pressure may be adjusted to within the range of 150–600 mOsm/kg. There is no particular limitation as to the osmotic compensating agent used but, for example, alkaline metal salts of propionic acid or the like and saccharides such as glucose and mannose are suitable. Alkali metal halides such as NaCl and alkali earth metal halides may be used as well provided that their percentage to all the anionic components in the reagent may be less than 50%. The osmotic compensating agents may be used as a combination thereof. When the osmotic pressure can be adjusted within a suitable range by the above-mentioned polyvalent anion and buffer, there is no need of containing the osmotic compensating agent.

The reagent of the present invention may also contain a cationic surfactant represented by the formula (IV) as a staining promoter.

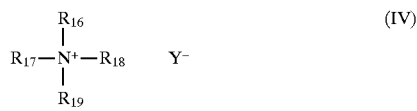

wherein $R_{16}$ is an alkyl group having 8–12 carbons; $R_{17}$, $R_{18}$ and $R_{19}$ are, the same or different, a lower alkyl group; and $Y^-$ is a halogen ion.

The alkyl group having 8–12 carbons in the formula may be a straight and branched chain alkyl group such as octyl, decyl or lauryl group. Among them, octyl and decyl group are preferred.

The lower alkyl group may be the same as $R_1$.

$Y^-$ is preferably chlorine ion or bromine ion.

Specific examples of the cationic surfactant are octyltrimethylammonium bromide (OTAB), decyltrimethylammonium bromide (DTAB), lauryltrimethylammonium chloride (LTAC), myristyltrimethylammonium bromide (MTAB) and cetyltrimethylammonium chloride (CTAC).

With respect to the concentration of the cationic surfactant which is a staining promoter, the effective concentration becomes lower as the total carbon number becomes more. For example, the suitable concentration may be 300–20,000 mg/liter to the reagent for OTAB, 500–3000 mg/liter for DTAB and 50–250 mg/liter for LTAC. The above staining promoters may be used as a combination thereof. The action mechanism of the cationic surfactant is not clear but is believed that the agent interacts with cell membrane of erythrocytes whereby the permeability of the dye is promoted. Therefore, the use of too much staining promoter is not preferred because the promoter damages the erythrocytes and, in some cases, causes hemolysis.

Furthermore, the cationic surfactant has the action of sphering the erythrocyte cells and, therefore, it can converge the intensity distribution of the forward scattered light of the population of the erythrocytes. As a result thereof, discrimination between thrombocytes and erythorocytic cells becomes easy. In addition, during the therapy of microcytosis such as iron deficiency anemia, both normocytic erythrocytes and microcytes caused by the disease are present in blood. In accordance with the reagent of the present invention, it has now become possible to discriminate between those erythrocytes by means of the front scatter light intensity. Moreover, elliptocytes which appear in small amount can be discriminated by the same manner too. As such, owing to the action of the cationic surfactant for sphering the erythrocytes, it is possible to measure reticulocytes and, at the same time, to detect the morphological abnormality of erythrocytes such as microcyte and elliptocyte as well.

Besides the above-mentioned components, the reagent of the present invention may further contain an antiseptic agent such as 2-pyridylthio-1-oxide sodium and β-phenethyl alcohol.

Furthermore, when the dyes which are used in the reagent of the present invention are unstable in an aqueous solution, the dyes can be stored by dissolving it in a suitable water-soluble nonaqueous solvent such as ethanol, dimethyl sulfoxide and ethylene glycol and, upon actual application, they may be used after mixing with an aqueous solution containing other components. Each of the dyes may be dissolved either in the same nonaqueous solvent or in different nonaqueous solvents.

The reagent of the present invention is particularly effective in the measurement of reticulocytes using a flow cytometer.

First, in step (1), the reagent for measuring reticulocytes in accordance with the present invention is mixed with a hematological sample for preparing a sample to be measured. The hematological sample may be any sample which contains blood components to be measured, such as bone marrow liquid or peripheral blood treated with an anticoagulant. Preferably, the sample to be measured is prepared by mixing the reagent for measuring reticulocytes with a hematological sample in a ratio of from 100:1 to 1,000:1 followed by reacting them. Reaction temperature at that time is suitably about 25°–50° C. or, more suitably, 35°–45° C. The suitable reaction time may vary depending upon the dyes contained in the reagent but, preferably, may be about from 10 seconds to five minutes, more preferably, about from 20 seconds to 2 minutes and, still more preferably, about from 20 to 60 seconds.

In step (2), the sample obtained in step (1) is introduced into a fluid system of a flow cytometer having a light source of red wave length. There is no particular limitation for the light source of red wave length so far as it can emit a light of a wavelength capable of exciting the dye used (fluorescence dye) such as a light source emanating a light having a wave length of about 600–680 nm. Its examples are a He/Ne laser, a semiconductor laser with a red wave length region and the like. Optical parts of the flow cytometer having the light source of red wave length used here are shown in FIG. 1. In front of a semiconductor laser 1, there is a flow cell via a condensing lens system 2 and, in front of a flow cell, there are a light-collecting lens 5 for forward scattered light and a photodiode 6 via a beam stopper 4. In addition, at the side of a flow cell 3, there are a band pass filter 8 and a photomultiplier tube 9 via a light-collecting lens 7 for a side fluorescence. With respect to other constructing parts such as a flowing part, data processing part, etc., the known parts or the like may be used after being modified.

In step (3), the above-mentioned light of red wave length is irradiated to the cells running in a sheath flow and, in step (4), scattered light and fluorescence emanated from the cells are measured. The scattered light at this time may be either forward or side scattered light and, moreover, the forward scattered light may be either forward low-angle scattered light (1°–5°) or forward high-angle scattered light (6°–20°). Although the scattered light is a parameter reflecting the cell size, another method for obtaining cell size information of the cell is an electric resistance method. In some cases, it is possible to measure an electric resistance signal by means of an electric resistance method instead of measuring the scattered light.

In step (5), platelets and other cells are discriminated by means of scattered light intensity or a scattergram of scattered light intensity and fluorescence intensity; in step (6), erythrocytes, reticulocytes and leukocytes are discriminated by means of fluorescence intensity or by means of a scattergram of fluorescence intensity and scattered light intensity; and, in step (7), erythrocytes and reticulocytes are classified and counted whereby their cell numbers and cell ratio are calculated.

It is also possible that reticulocytes are classified and counted for each degree of their maturation or, to be more specific, by means of a difference in the fluorescence intensity whereby each of their percentage in the total reticulocytes can be calculated.

EXAMPLE 1

A reagent for measuring reticulocytes having the following composition was prepared.

| | |
|---|---|
| Dye A for specifically staining reticulocytes | 3 mg |
| Dye B for specifically staining the leukocytes | 0.03 mg |
| Tricine (buffer) | 1.79 g |
| Trisodium citrate dihydrate (polyvalent anion) | 29.4 g |
| LTAC (cationic surfactant; staining promoter) | 50 mg |
| Pure water | 1 liter |

(Adjusted to pH 9.0 using sodium hydroxide)

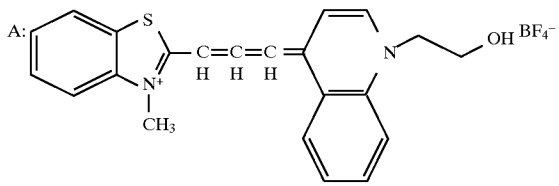

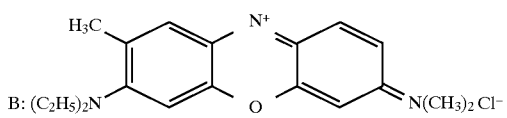

Figure 2:
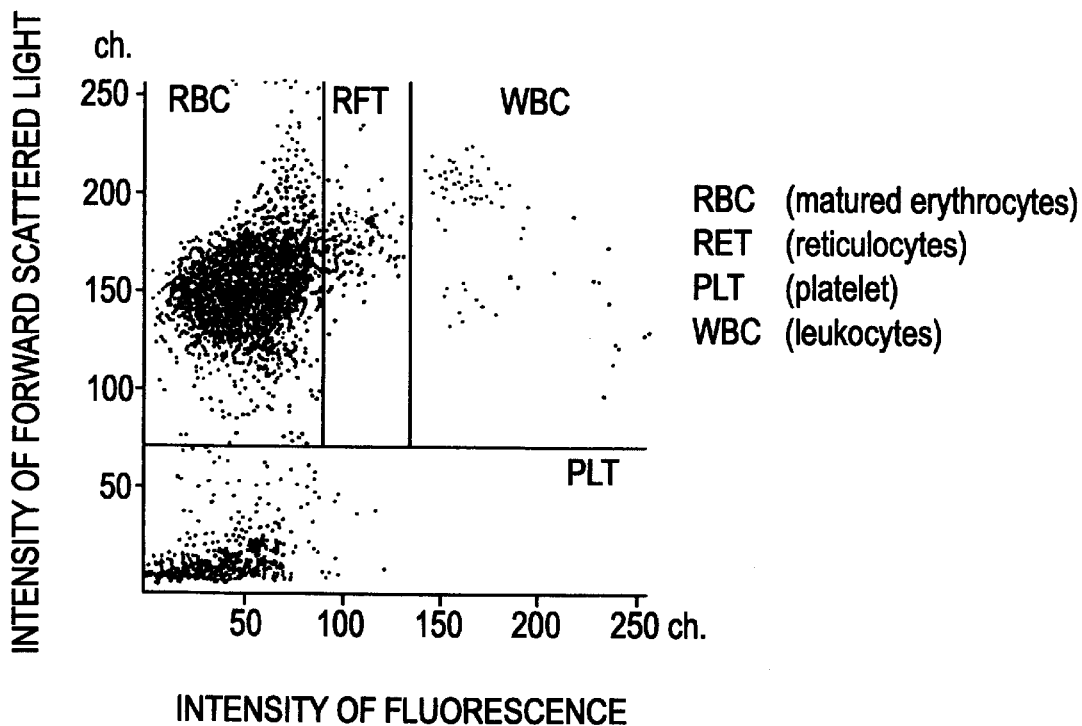
FIG. 2 is a scattergram representing forward scattering light intensity and fluorescence intensity of a peripheral blood sample from a normal and healthy person measured using a reagent for measuring reticulocytes in accordance with the present invention containing a dye A which specifically stains reticulocytes and another dye B which specifically stains the leukocytes.

Blood (10 μl) of a normal and healthy person treated with an anticoagulant agent was mixed with 2 ml of the reagent followed by incubating at 40° C. for 120 seconds. Forward scattered light intensity and fluorescence intensity were measured for the above-prepared sample using an optical system as shown in FIG. 1. Referring to a scattergram as shown in FIG. 2, the reticulocyte ratio was 2.0%. As a control, the sample was also measured conducted using an apparatus R-2000 (manufactured by Toa Medical Electronics Co., Ltd.) whereupon the result was 2.0%.

Figure 3:
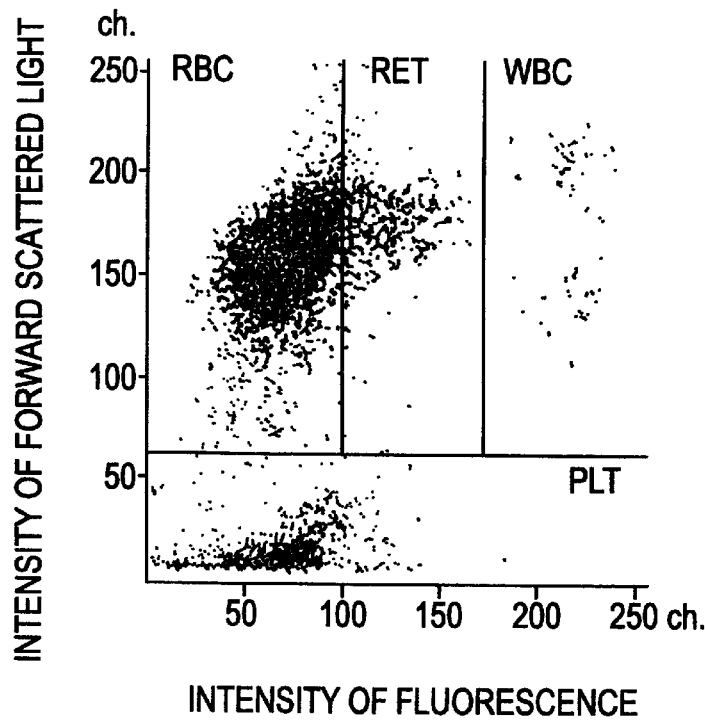
FIG. 3 is a scattergram representing forward scattering light intensity and fluorescence intensity of a peripheral blood sample of a patient having abnormal lymphocytes measured using a reagent for measuring reticulocytes in accordance with the present invention containing a dye A which specifically stains reticulocytes and another dye B which specifically stains the leukocytes.

Blood containing lymphocytic abnormal cells was measured by the same manner whereupon a scattergram of FIG. 3 was obtained. In this scattergram, it was possible to clearly discriminate between a population of reticulocytes and a population of leukocytes.

EXAMPLE 2

A reagent for measuring reticulocytes having the following composition was prepared.

| | |
|---|---|
| Dye A for specifically staining reticulocytes | 3 mg |
| Dye C for specifically staining the leukocytes | 30 mg |
| Tricine (buffer) | 1.79 g |
| Trisodium citrate dihydrate | 29.4 g |
| LTAC | 150 mg |
| Pure water | 1 liter |

(Adjusted to pH 9.0 using sodium hydroxide)

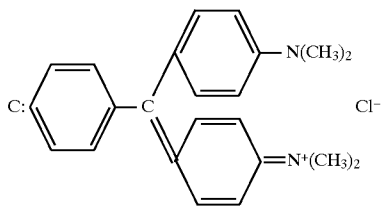

Basic Green 4 (CI No. 42,000)

Figure 4:
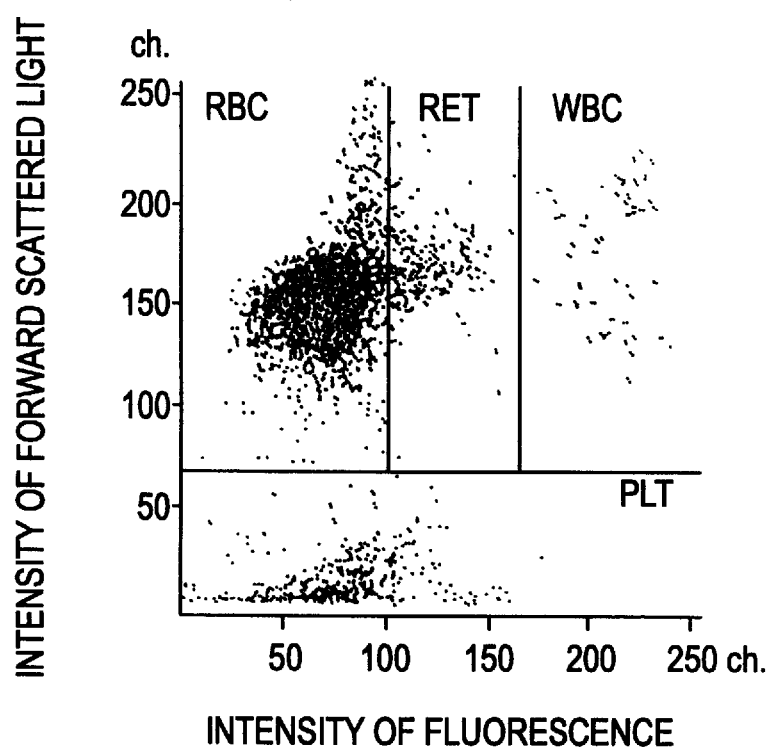
FIG. 4 is a scattergram representing forward scattering light intensity and fluorescence intensity of a peripheral blood sample of a normal and healthy person measured using a reagent for measuring reticulocytes in accordance with the present invention containing a dye A which specifically stains reticulocytes and another dye C which specifically stains the leukocytes.

Blood (10 μl) of a normal and healthy person treated with an anticoagulant agent was mixed with 2 ml of the reagent followed by incubating at 40° C. for 120 seconds. Forward scattered light intensity and fluorescence intensity were measured for the above-prepared sample using an optical system as shown in FIG. 1. Referring a scattergram as shown in FIG. 4, the reticulocyte ratio was 1.8%. As a control, the sample was also measured using an apparatus R-2000 (manufactured by Toa Medical Electronics Co., Ltd.) whereupon the result was 1.7%.

Comparative Example 1

A reagent for measuring reticulocytes having the following composition was prepared.

| | |
|---|---|
| Dye A for specifically staining reticulocytes | 3 mg |
| Tricine (buffer) | 1.79 g |
| Trisodium citrate dihydrate | 29.4 g |
| LTAC | 150 mg |
| Pure water | 1 liter |
| (Adjusted to pH 9.0 using sodium hydroxide) | |

Figure 5:
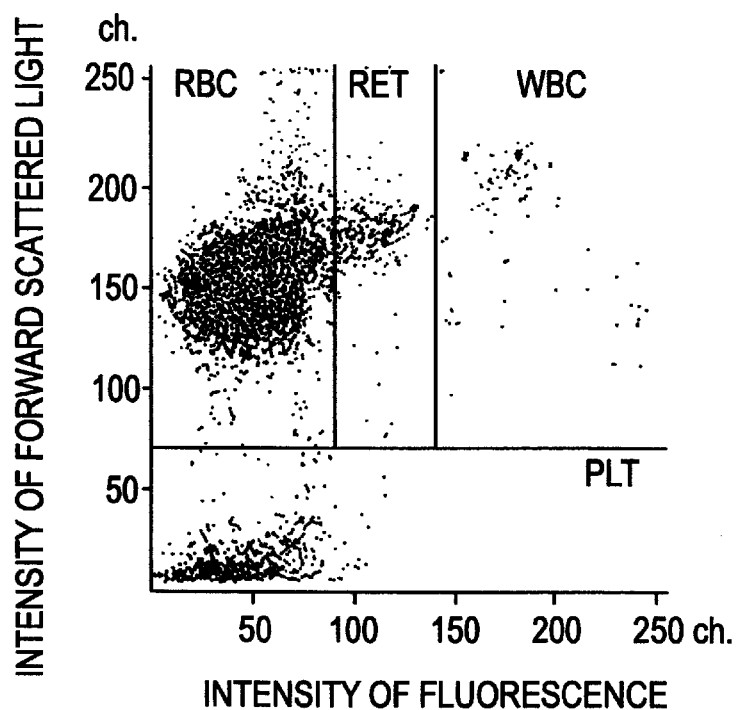
FIG. 5 is a scattergram representing forward scattering light intensity and fluorescence intensity of a peripheral blood sample of a normal and healthy person measured using a reagent for measuring reticulocytes containing only a dye A which specifically stains reticulocytes.

Blood (10 μl) of a normal and healthy person treated with an anticoagulant agent was mixed with 2 ml of the reagent followed by incubating at 40° C. for 120 seconds. Forward scattered light intensity and fluorescence intensity were measured for the above-prepared sample using an optical system as shown in FIG. 1. Referring to a scattergram as shown in FIG. 5, the reticulocyte ratio was 2.1%. As a control, the sample was also measured using an apparatus R-2000 (manufactured by Toa Medical Electronics Co., Ltd.) whereupon the result was 2.0%.

Figure 6:
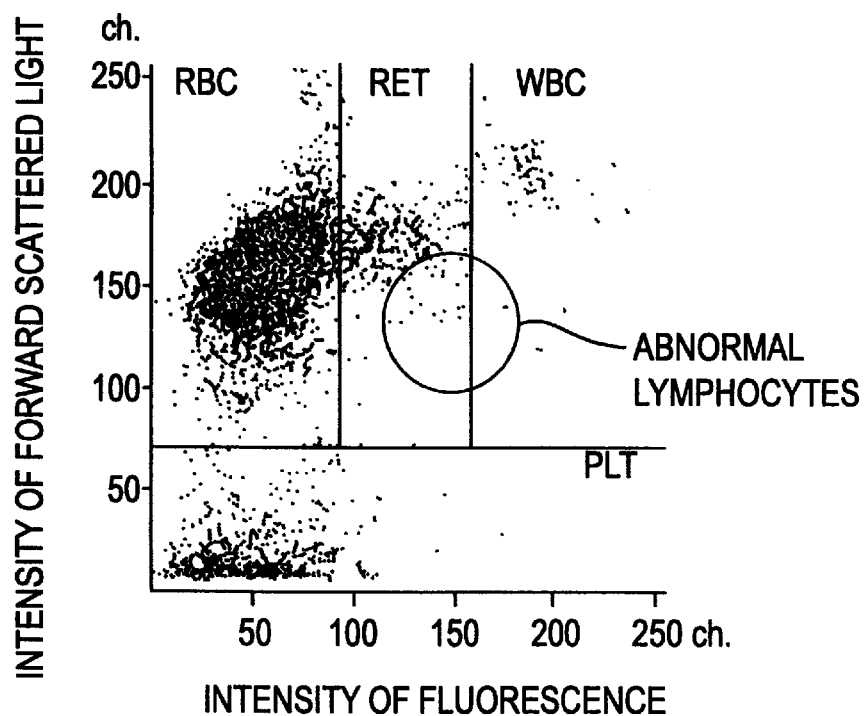
FIG. 6 is a scattergram representing forward scattering light intensity and fluorescence intensity of a peripheral blood sample of a patient having abnormal lymphocytes measured using a reagent for measuring reticulocytes containing only a dye A which specifically stains reticulocytes.

Blood containing lymphocytic abnormal cells was measured by the same manner whereupon a scattergram of FIG. 6 was obtained. In this scattergram, a clear discrimination was not possible between a population of reticulocytes and a population of leukocytes.

In accordance with the reagent and the measuring method of the present invention, reticulocytes can be accurately and quickly measured by means of a flow cytometer using a cheap and small light source even in the case of special samples containing abnormal lymphocytes or the like. Thus, in accordance with the reagent and the measuring method of the present invention, the fluorescence intensity only of leukocytes can be promoted in a sample containing abnormal lymphocytes or the like without changing the fluorescence intensities of matured erythrocytes and reticulocytes whereby it has now become possible to accurately classify and count reticulocytes.

What is claimed is:

1. A reagent for measuring reticulocytes comprising at least one dye which specifically stains leukocytes so as to differentiate reticulocytes from leukocytes and at least one dye which specifically stains reticulocytes selected from the group consisting of formula (I),

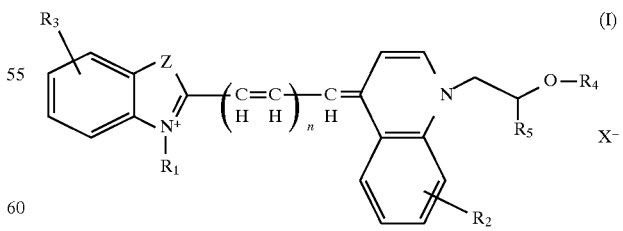

wherein $R_1$ is a hydrogen atom or a lower alkyl group; $R_2$ and $R_3$ are, the same or different, hydrogen atom, a lower alkyl or lower alkoxy group; $R_4$ is hydrogen atom, an acyl or lower alkyl group; $R_5$ is hydrogen atom or an optionally substituted lower alkyl group; Z is sulfur atom, oxygen atom, or carbon atom substituted with a lower alkyl group; n is 1 or 2; and X⁻ is an anion, formula (II'),

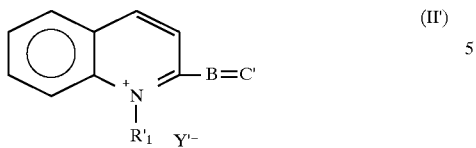

wherein B is selected from the group consisting of —(CH=CH)$_{n'}$—CH=, where n' is 0, 1 or 2 and —CH=C(—R$_4$') —CH=; C' is selected from the group consisting of

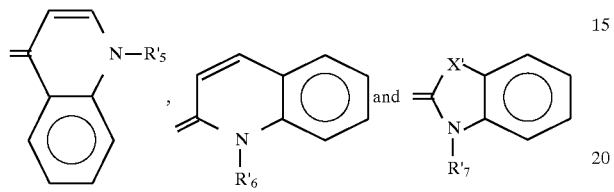

X' is selected from the group consisting of O, S, Se and —C(CH$_3$)$_2$; Y' is selected from the group consisting of Cl, Br and I; and R$_1$', R$_4$', R$_5$', R$_6$' and R$_7$' are, the same or different and selected from the group consisting of a lower alkyl, a lower alkenyl and a halogenated lower alkyl; and formula (III'),

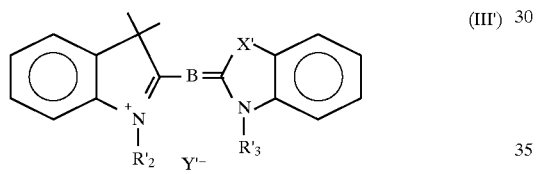

wherein B, X', and Y'⁻ are as in formula (II') and, R$_2$' and R$_3$', are the same or different and selected from the group consisting of a lower alkyl, a lower alkenyl and a halogenated lower alkyl.

2. A reagent for measuring reticulocytes according to claim 1 wherein the at least one dye which specifically stains reticulocytes is selected from the group consisting of 1,1',3,3,3',3'-hexamethylindodicarbocyanine iodide, 1,1'-diethyl-2,4'-quinocarbocyanine iodide, pinacyanol chloride and 1,3'-diethyl-2,2'-quinothiacarbocyanine iodide.

3. A reagent for measuring reticulocytes according to claims 1 in which the at least one dye which specifically stains leukocytes is represented by the formula (II):

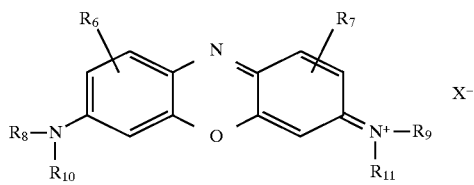

wherein R$_6$ and R$_7$ are, the same or different, hydrogen atom, a lower alkyl, lower alkoxy or phenyl group; R$_8$ to R$_{11}$ are, the same or different, hydrogen atom or a lower alkyl group; and X is an anion or by the formula (III):

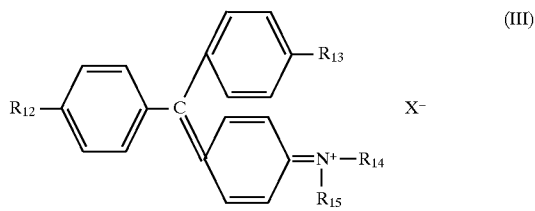

wherein R$_{12}$ and R$_{13}$ are, the same or different, hydrogen atom, a lower alkyl, lower alkoxy group or a lower-alkyl-substituted amino group; R$_{14}$ and R$_{15}$ are, the same or different, hydrogen atom or a lower alkyl group; and X⁻ is an anion.

4. A reagent for measuring reticulocytes according to claim 1 further comprising a polyvalent anion for inhibiting a nonspecific fluorescence of erythrocytes.

5. A reagent for measuring reticulocytes according to claim 1 further comprising a buffer for adjusting pH.

6. A reagent for measuring reticulocytes according to claim 1 further comprising an osmotic compensating agent for adjusting an osmotic pressure of the reagent within a physiologically normal range.

7. A reagent for measuring reticulocytes according to claim 1 further comprising a staining promoter.

8. A reagent for measuring reticulocytes according to claim 7 in which the staining promoter is a cationic surfactant.

9. A reagent for measuring reticulocytes according to claim 8 in which the cationic surfactant is represented by the formula (IV):

wherein R$_{16}$ is an alkyl group having 8–12 carbons; R$_{17}$, R$_{18}$ and R$_{19}$ are, the same or different, a lower alkyl group; and Y⁻ is a halogen ion.

10. A reagent for measuring reticulocytes according to claim 9 in which the cationic surfactant is at least one selected from the group consisting of laurytrimethylammonium chloride, decyltrimethylammonium bromide and octyltrimethylammonium bromide.

11. A method for measuring reticulocytes using the reagent as defined in claim 1.

12. A method according to claim 11 in which a flow cytometer is used.

* * * * *

UNITED STATES PATENT AND TRADEMARK OFFICE
CERTIFICATE OF CORRECTION

PATENT NO. : 5,891,731
DATED : April 6, 1999
INVENTOR(S) : Yasumasa AKAI, et al.

It is certified that error appears in the above-identified patent and that said Letters Patent is hereby corrected as shown below:

In claim 1, column 13, line 23, before "X'"insert --where--; and in line 24, change "Y'" to --Y'--.

In claim 3, line 48, change "claims" to --claim--; and in column 14, line 2, change "X" to --X'--.

Signed and Sealed this

Seventh Day of September, 1999

Attest:

Q. TODD DICKINSON

Attesting Officer

Acting Commissioner of Patents and Trademarks